United States Patent [19]

Koka et al.

[11] Patent Number: 4,751,644
[45] Date of Patent: Jun. 14, 1988

[54] INTERLEAVED SOURCE FAN RECONSTRUCTION TECHNIQUE

[75] Inventors: Narasimharao Koka, Richmond Hts.; Heang K. Tuy, Cleveland; Gordon D. DeMeester, Wickliffe; Rodney A. Mattson, Mentor, all of Ohio

[73] Assignee: Picker International, Inc., Highland Hts., Ohio

[21] Appl. No.: 792,069

[22] Filed: Oct. 28, 1985

[51] Int. Cl.$^4$ ............................................. G06F 15/42
[52] U.S. Cl. .................................... 364/414; 378/150; 378/8
[58] Field of Search ...................... 364/414, 200, 900; 378/152, 150, 4, 901, 8

[56] References Cited

U.S. PATENT DOCUMENTS

| | | | |
|---|---|---|---|
| 4,135,247 | 1/1979 | Gordon | 364/414 |
| 4,182,311 | 1/1980 | Seppi | 378/8 |
| 4,206,360 | 6/1980 | LeMay | 250/445 T |
| 4,295,195 | 10/1981 | Hounsfield | 364/414 |
| 4,365,339 | 12/1982 | Pavkovich | 378/15 |
| 4,504,909 | 3/1985 | Acharya | 364/414 |
| 4,547,892 | 10/1985 | Rickey | 378/8 |
| 4,610,021 | 9/1986 | Peschmann | 378/152 |
| 4,630,202 | 12/1986 | Mori | 364/414 |
| 4,639,941 | 1/1987 | Hounsfield | 364/414 |
| 4,656,584 | 3/1987 | Katsumata | 364/414 |
| 4,665,539 | 5/1987 | Geluk | 364/414 |

OTHER PUBLICATIONS

"AS&E CT Scanner", AS&E Inc.
"Current Status of Cardiovascular Imaging by Transmission Computed Tomography", W. R. Brody, 1978, pp. 48-55.
"Dynamic Computed Tomography for the Heart", Taneno et al., pp. 77-84, Nat. Inst. Rad. Sci., Japan, 1977.

Primary Examiner—Michael R. Fleming
Attorney, Agent, or Firm—Fay, Sharpe, Beall, Fagan, Minnich & McKee

[57] ABSTRACT

In a fourth generation CT scanner, source views or data sets are generated for reconstruction processing. A fan beam (16) of radiation rays is rotated around an image region (12) to irradiate subsets of detectors of a detector ring (10). A data sampler (B) samples the detectors of each irradiated subset a plurality of times, each time with the radiation fan beam displaced incrementally from the preceding time to generate a plurality of the source views or data sheets from the same detectors. A plurality of consecutive source views or data sets are interleaved to produce a signal interleaved view or data fan. More specifically, the data sets are stored in data set memories (20-26) and interleaved serially into a data fan memory (30). Each time the fan beam rotates sufficiently to irradiate a different detector subset, an additional plurality of data sets are generated and interleaved into another data fan. The data fans are reconstructed (E) into a representation of an image of radiation absorptive properties of an object disposed in the image region. This reconstruction method is especially applicable to cardiac synchronization or gated patient scanning. This method improves the dynamic scan capacity of fourth generation scanners, improves tolerance to detector drifts, and improves tolerance to temporal x-ray fluctuations.

20 Claims, 3 Drawing Sheets

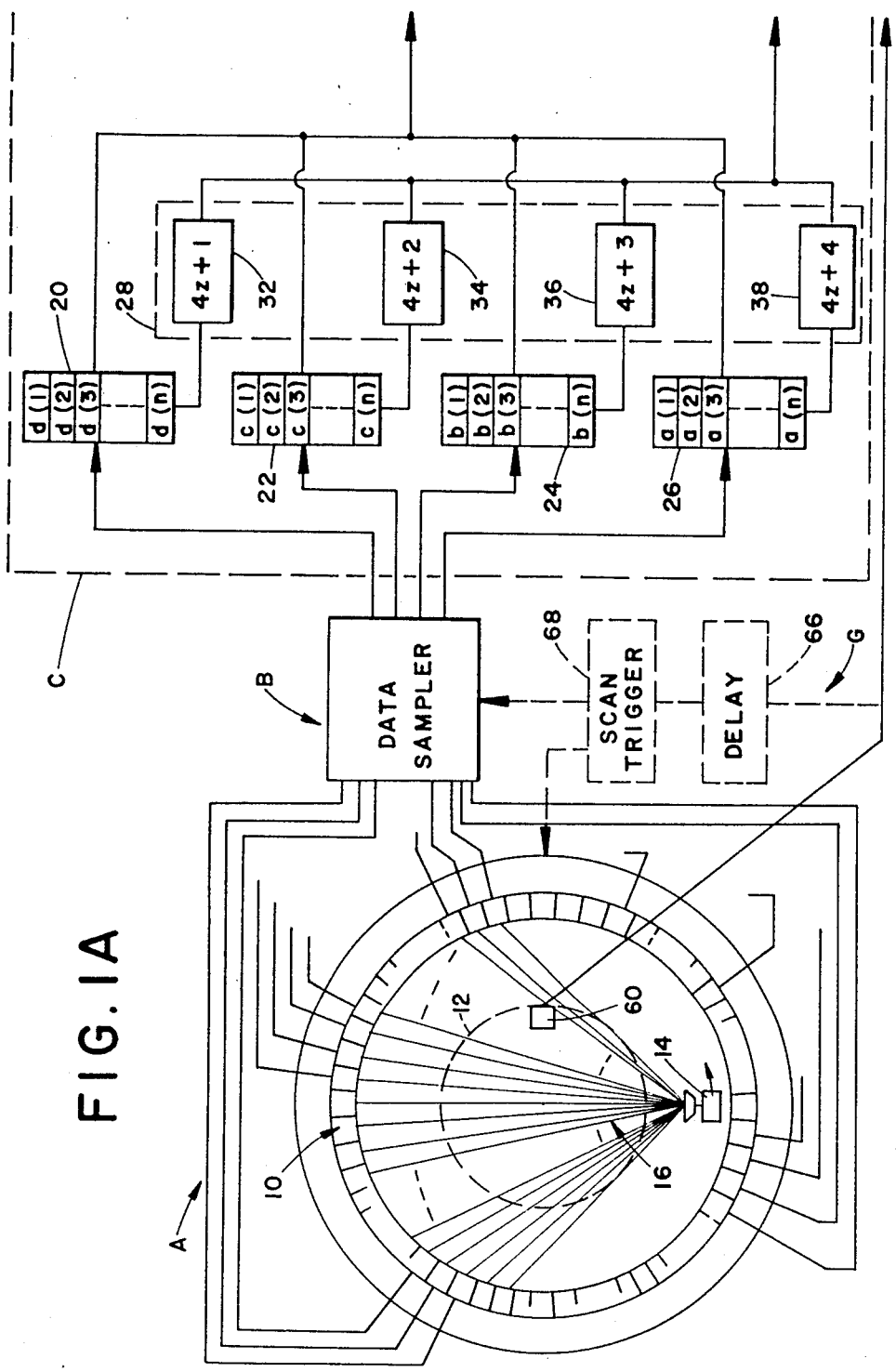
FIG. IA

INTERLEAVED SOURCE FAN RECONSTRUCTION TECHNIQUE

BACKGROUND OF THE INVENTION

The present invention relates to the tomographic scanner and image reconstruction arts. The invention finds particular application in fourth generation computerized tomographic scanners and will be described with particular reference thereto.

Tomographic scanners have progressed from traverse and rotate early generation scanners to purely rotational later generation scanners. In one of the purely rotational tomographic scanners, commonly known as a third generation scanner, a source of fan beam radiation and an arc of radiation detectors rotate concurrently around an image region or scan circle. The third generation image reconstruction process assumes that the data in each view sampling results from concurrently occurring x-ray projections or rays. Each ray or projection extends from an apex at the x-ray tube focal spot to one of the detectors. The sampling of a fan of concurrent rays or projections with a common apex or position of the x-ray source constitutes a single view for the reconstruction process. Data collected in this fashion are commonly referred to as "source fan data".

In third generation scanners, the ray sampling is limited by the number of active detectors per view. The view sampling is limited by the data acquistion rate of the system. The faster data can be acquired, the more rapidly views can be sampled.

A fourth generation tomographic scanner has an annular array of detectors circumscribing the image region. A radiation fan beam source orbits around the image region to irradiate continuously shifting subsets of the stationary detector ring until the required amount of data is acquired. The image reconstruction algorithm uses each detector as the origin of a fan. Thus, the radiation rays or projections in each view or fan occur at different intervals in time as the source rotates to irradiate each detector from a plurality of directions. Rays are defined by the projections of radiation between the source and the active detectors during the periods of time when the outputs of the detectors are being sampled. Each detector is sampled a plurality of times as the radiation source sweeps opposite the image region from the detector to generate each view. The ray sampling is limited by the data acquisition rate of the system. View sampling is limited by the number of detectors in the ring.

The faithful reconstruction of images and the susceptibility to artifacts are trade-offs in both third and fourth generation scanners. Third generation scanners commonly have more detectors irradiated at a time. If ray samplings were performed in a fourth generation scanner in the same manner as in a third generation scanner, the resolution would be limited by the smaller number of detectors in the ring which are viewed at one time. A fourth generation scanner detector ring commonly contains about 1200 to 1500 detectors, with approximately 256 detectors viewed at any one time.

Increasing the number of detectors in the ring of fourth generation scanners could improve performance. However, increasing the number of detectors would increase the complexity of the system.

The present invention contemplates a new and improved tomographic scanner imaging modality. A fourth generation scanner is adapted to acquire data in a manner which is better suited for gated scanning. Source fan data is generated which has a ray sampling that is substantially equivalent to third generation scanners.

SUMMARY OF THE INVENTION

In accordance with one aspect of the present invention, a method of tomographic examination is provided. A fan of penetrating radiation which spans an image region is rotated therearound. The radiation which has traversed the image region is received with a ring of detectors that at least partially surround the image region. A preselected subset of the detectors are irradiated at one time. Each irradiated subset of the detectors is sampled a plurality of times during the time which it is irradiated to generate a plurality of sets of electronic data. The plurality of data sets corresponding to said irradiated subset of detectors are interleaved to generate a data fan. A representation of an image of radiation absorptive properties of an object in the image region is reconstructed from a plurality of the data fans.

In accordance with another aspect of the present invention, a tomographic scanning apparatus is provided. A ring of detectors at least partially surrounds an image region. A radiation source which produces a fan of penetrating radiation is mounted to irradiate the image region with a fan beam of radiation. A rotating means selectively rotates the fan beam relative to the detector ring such that the fan beam selectively irradiates each of a plurality of subsets of the detectors. A detector sampling means samples each irradiated subset of the detectors a plurality of times during the time which each subset is irradiated. An interleaving means selectively interleaves the data sets generated from each detector subset to reorganize the plurality of data sets into a single data fan. An image reconstruction means reconstructs the data fans collected from a plurality of different detector subsets into a representation of an image of radiation absorptive properties of an objectd in the image region.

One advantage of the present invention is that it enables scans to be made with short gating periods or pulsed x-rays.

Another advantage of the present invention is that it enables shorter reconstruction times. Reconstruction processing can commence as soon as acquisition of one view is completed.

Yet other advantages reside in an improved dynamic scan capability and greater tolerance to x-ray temporal fluctuations.

Another advantage of the present invention relative to fourth generation scanners resides in a high performance dynamic scan capability that is amenable to gated scanning without increasing the number of detectors.

A further advantage is provision for a hybrid scanner mode that is more tolerant to detector drifts than third generation scanners and more tolerant to temporal x-ray fluctuations than conventional fourth generation scanners.

Moreover, the present invention would be advantageous in multiple x-ray tube and slip ring (continuously rotating) fourth generation scanners in reducing scan times. Reconstruction of events that occur in a period of 100 to 200 milliseconds may be permitted.

Still further advantages will be apparent to those of ordinary skill in the art upon reading and understanding the following detailed description of the preferred embodiment.

BRIEF DESCRIPTION OF THE DRAWINGS

The invention may be embodied in various steps and arrangements of steps and various components and arrangements of components. The drawings are only for purposes of illustrating a preferred embodiment and are not to be construed as limiting the invention.

FIGS. 1A and 1B taken together are a diagrammatic illustration of a tomographic scanner in accordance with the present invention;

DETAILED DESCRIPTION OF THE PREFERRED EMBODIMENT

Figure 1B:
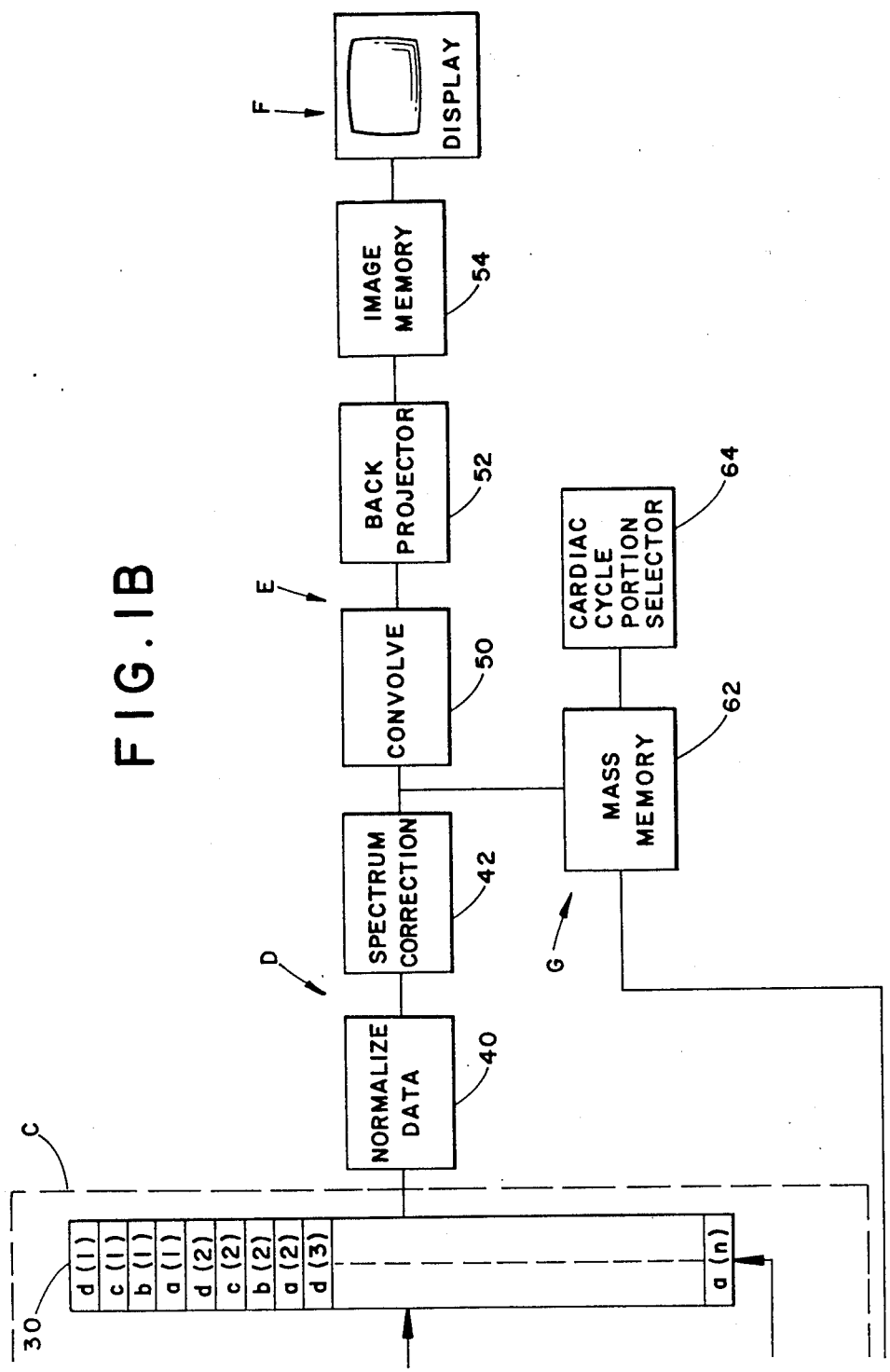

With reference to FIGS. 1A and 1B, a fourth generation tomographic scanner gantry A irradiates an examined object and generates electronic data signals indicative of radiation absorptive or transmissive properties thereof. A data sampling means B samples the data generated by the detectors to generate a plurality of data sets. In the preferred embodiment, each data set includes a data element for each detector which is currently irradiated and sampled. The sampling means samples an irradiated detector subset a plurality of times before the next subset or fraction of detectors becomes irradiated. An interleaving means C interleaves the plurality of data sets which correspond to each common subset of the detectors during the plural samplings thereof to generate a data fan for each detector subset. Each data fan is normalized and spectrum and other corrections or adjustments are made thereto by a data correcting means D. An image reconstruction means E reconstructs a representation of the radiation absorptive properties of an examined object from the fan beam data for display on a display means F, storage on tape or disc memory, or the like. A cardiac synchronization means G synchronizes the scanning with the patient's cardiac cycle. In one embodiment, the cardiac synchronization means initiates a scan and data collection at a preselected phase in the cardiac cycle. In another embodiment, data is collected for all phases of the cardiac cycle and stored. Only data corresponding to a selected phase in the cardiac cycle is retrieved for use in an image reconstruction.

The gantry A includes a circular ring of detectors 10 which at least partially encircle an image region or scan circle 12. In the preferred embodiment, the detector ring includes 1200 detectors which completely encircle the image region. However, it is to be appreciated that a greater or lesser number of detectors may be utilized. In some applications, the detectors may only partially encircle the image region. A radiation source 14 generates a fan beam of radiation 16 which spans and is tangent to the image region 12. More specific to the preferred embodiment, the fan beam includes a fan of discrete rays of radiation. The radiation fan beam passes through the image region and impinges on a fraction or subset of the detectors of the ring. In the preferred embodiment, the irradiated detector subset includes 256 detectors when scanning a patient's body and 128 detectors when scanning the head. A rotating means (not shown) rotates the fan beam relative to the detector ring. In the preferred embodiment, the radiation source is rotated while the detector ring remains stationary. However, it is to be appreciated that the detector ring may be rotated relative to the source, the radiation source and ring may both be rotated, a multiplicity of x-ray tubes may be provided or other structures may be utilized which cause relative rotational movement between the radiation fan beam and the detectors.

The data sampling means B samples the subset of radiation detectors which are irradiated by the radiation beam at one time. More specifically, the data sampling means samples each radiation detector of the irradiated subset substantially simultaneously to generate a first data set or view. The data sampling means samples the same detector subset a plurality of times before the radiation source rotates sufficiently for the irradiated detector subset to change by one detector. In the preferred embodiment, the data sampling means samples the irradiated 256 detector body examining subset four times before the irradiated detector subset changes. When irradiating a 128 detector head examining subset, each detector subset is preferably sampled eight times.

Figure 2:
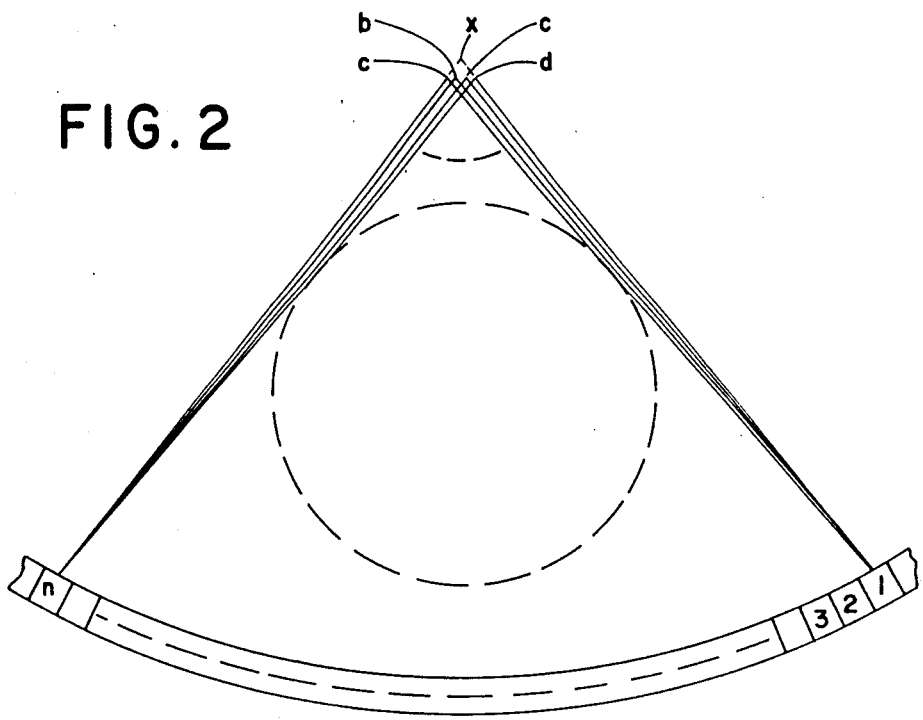
FIG. 2 is a diagrammatic illustration which respresents sampling a subset of detectors 1 through n with the source at each of positions a, b, c, and d; and, FIG. 3 is a diagrammatic illustration of a data fan produced by interleaving the data of FIG. 2 in accordance with the present invention.

With reference to FIG. 2 and continuing reference to FIGS. 1A and 1B, the radiation source 14 is rotating counterclockwise through positions d, c, b, and a. For a plurality of samplings, the radiation fan beam 16 impinges on detectors 1 through n, where n is 256 in the preferred embodiment. As the radiation source assumes each of positions d, c, b, a, the sampling means causes detectors 1 through n to be sampled. The first time detectors 1 through n are sampled, when the source is at position d, a first data set consisting of n data elements is produced and stored in a first n dimensional data set memory 20 of the interleaving means C. When the radiation source has moved to position c, the sampling means samples detectors 1 through n a second time and stores the data elements of the second data set in a second data set memory means 22 of the interleaving means. Analogously, when the source is at position b, the detectors are sampled a third time and data elements are stored in a third data set memory 24 of the sorting means. When the source is at position a, the detectors are sampled a fourth time and the n dimensional data set is stored in a fourth data set memory means 26. Analogously, the detectors may be sampled additional times and stored in further data set memory means of the interleaving means C.

Figure 3:
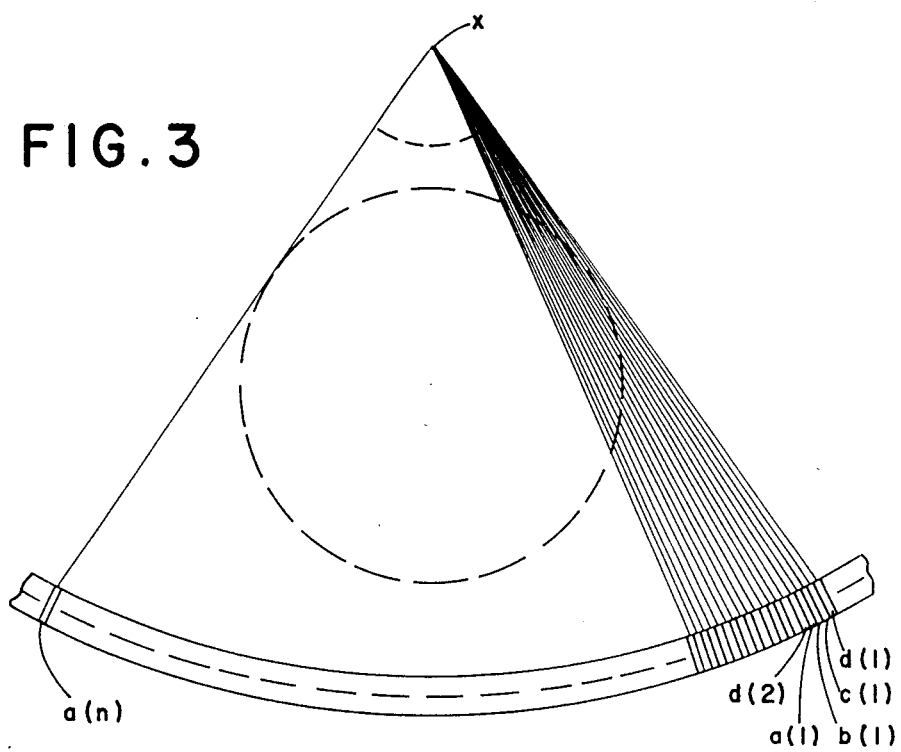

With reference to FIG. 3 and continuing reference to FIGS. 1A and 1B, the interleaving means C includes an addressing means 28 which causes data elements from each of the data set memories 20-26 to be transferred in a preselected, interleaved order into a data fan memory 30.

In the preferred embodiment in which the sampling means samples each irradiated detector subset four times, a first addressing means 32 places the data elements from the first data set memory 20 at every fourth memory address of the data fan memory 30, that is, every $4z+1$st address position, where z is an integer from zero to $n-1$. For example, the data element sampled at the first detector 1 when the source was at position d is channelled into a first address of the data fan memory 30. The data element sampled at the second detector 2 when the source was at position d is channelled to the fifth data fan memory adress, and so forth. In the general case in which s data sets or views are to be interleaved, the data elements are placed at every $sz+1$st address of the data fan memory 30.

A second addressing means 34 causes each element of the second data set memory 22 to be channelled serially into every fourth address of the fan data memory 30, i.e., each $4z+2$nd memory address, where z is the integers from zero through $n-1$. For example, when the source was at position c, the data element sampled at the first detector 1 is channelled to the second data fan memory address; the data element from detector 2 is channelled to the sixth address; and so forth.

A third addressing means 36 causes each data element of the third data set memory 24 to be channelled serially into every fourth memory address of the fan beam 30, i.e., each $4z+3$rd memory address where z is the integers from zero through $n-1$. For example, the data element sampled at the first detector 1 when the source was at position b is channelled to the third memory position or address of the data fan memory 30. The data element from the second detector sampled with the source at position b goes to the seventh fan beam memory address, etc.

A fourth addressing means 38 causes the memory data elements of the fourth data set memory 26 to be channelled serially into every fourth memory address of the data fan memory 30, i.e., every $4z+4$th where z is the integers from zero through $n-1$. For example, with the source at position a, the data element sampled at the first detector 1 goes to the fourth data fan memory position, the data element from the second detector 2 goes to the eighth memory position, and so forth. In this manner, a data fan of the configuration of FIG. 3 is generated.

In this manner, four data sets or views are sampled. The first data set represents radiation attenuation along rays $d(1), d(2), \ldots d(n)$. The second data set represents radiation attenuation along rays $c(1), c(2), \ldots c(n)$. The third data set represents attenuation along rays $b(1), b(2), \ldots b(n)$. The fourth data set represents attenuation along rays $a(1), a(2), \ldots a(n)$. Note FIG. 2. The interleaving means C interleaves the four data sets of the preferred embodiment into a single data set or data fan representing radiation attenuation along rays $d(1), c(1), b(1), a(1), d(2), c(2), b(2), a(1), d(3), \ldots d(n), c(n), b(n), a(n)$, Note FIG. 2.

The above described serial transfer of data elements from four data sets is provided by way of illustration only. It is to be appreciated that other numbers of data sets may be interleaved or other interleaving or sorting patterns may be implemented.

After the four data sets are sampled and stored in the data set memories 20-26, the source rotates sufficiently that the next detector subset is irradiated. In the example, the next detector subset will be detectors 2 through $n+1$. The process of sampling the data from this second detector subset a plurality of times is repeated. The second plurality of data sets are interleaved into a second data fan. This procedure is then repeated for each of the available subsets of detectors.

Referring again to FIGS. 1A and 1B, the data correction means D includes a data normalizing means 40 which normalizes the data elements of the data fan as is conventional in the art. A spectrum correction means 42 of conventional design provides a beam hardness correction on the data fans.

The image reconstruction means E includes a convolver 50 which convolves each data fan with a convolution function, again as is conventional in the art. A back projector 52 back projects the convolved data fans into an image memory 54. The conventional back projection algorithms project data based on the geometry of the system, including the apex X of the fan beams which functions as the origin of the system. With reference to FIG. 2, the effective origin of the fan beam in the present invention is the projection of the divergent extremities of the fan beam, i.e. the rays from position d to detector i.e. d(1) and from position a to detector n, i.e. a(n). Thus, the conventional back projection algorithm is modified to change the origin from the distance of points, a, b, c or d from the center of the scan circle to the effective origin at point X.

In one embodiment, the cardiac synchronizing means G retrospectively gates the data to select an imaged portion of the cardiac cycle. A QRS detector 60 or other appropriate means monitors the scanned patient's cardiac cycle. Each interleaved data fan or view is stored with the portion of the cardiac cycle which it represents in a mass memory means 62. After the patient has been scanned for several cardiac cycles, a portion of the cardiac cycle to be imaged is selected by an appropriate entry on a cardiac cycle portion selection means 64. The cardiac portion selection means retrieves the stored views which correspond to the selected portion of the cardiac cycle for reconstruction into an image by the image reconstruction means E.

Alternately, the cardiac synchronizing means G may utilize a prospective gating scheme. The QRS detector 60 or other appropriate means detects a preselected trigger point in the scanned patient's cardiac cycle. A delay means 66 causes a preselected delay from the cardiac cycle trigger point until initiation of a scan for several degrees of arc by a scan triggering means 68. Data from a plurality of views during which the x-ray system is active are collected and interleaved during a preselected portion of the cardiac cycle to be imaged. The scanning process is repeated in subsequent cardiac cycles to generate additional interleaved views from different angles for reconstruction into an image representation.

The invention has been described with reference to the preferred embodiment. It is to be appreciated that the above described functions and means may be performed by an appropriately programmed computer or processor, by dedicated modules, or by a combination thereof. Obviously, modifications and alterations will occur to others upon reading and understanding the preceding detailed description of the preferred embodiment. It is intended that the invention be construed as including as all such alterations and modifications in so far as they come within the scope of the appended claims or the equivalents thereof.

Having thus described a preferred embodiment, the invention is now claimed to be:

1. A method of tomographic examination comprising:
    rotating a fan of penetrating radiation around a spanned image region;
    receiving radiation which has traversed the image region with a ring of detectors which at least partially surround the image region, a subset of contiguous detectors being irradiated concurrently by radiation which has traversed the image region;
    as the fan of penetrating rotation rotates but before the fan rotates sufficiently to irradiate another detector subset, sampling each irradiated subset of detectors a plurality of times to generate a plurality of sets of electronic data from each detector subset, each set of electronic data representing different radiation paths through the image region;

interleaving the plurality of data sets corresponding to a common detector subset to generate a single interleaved data fan in which data is arranged in order by detector and data corresponding to a common detector is arranged in order by sampling time;

reconstructing a representation of an image of radiation absorptive properties of an object in the image region from a plurality of the data fans.

2. The method as set forth in claim 1 wherein the radiation fan is rotated continuously around the image region.

3. The method as set forth in claim 2 wherein the detector ring is stationary.

4. The method as set forth in claim 3 wherein the sampling of irradiated detectors is synchronized with a selected portion of a scanned patient's cardiac cycle.

5. The method as set forth in claim 1 wherein the sampling step further includes:

sampling each detector subset, which subsets include n detectors, substantially simultaneously to generate a first data set;

storing the first data set;

sampling the same detector subset a second time to generate a second data subset;

storing the second data set; and, wherein the interleaving step includes interleaving data elements of the stored first and second data sets alternately to generate the data fan.

6. The method as set forth in claim 5 wherein the sampling step further includes:

after the step of storing the second data set, sampling the detector subset a third time to generate a third data set;

storing the third data set; and, wherein the interleaving step includes interleaving data elements of the first, second, and third data sets serially.

7. The method as set forth in claim 6 wherein the sampling step further includes:

after the step of storing the third data set, sampling the detector subset a fourth time to generate a fourth data set;

storing the fourth data set; and, wherein the interleaving step includes interleaving data elements of the first, second, third, and fourth data sets serially.

8. The method as set forth in claim 1 wherein an origin of the fan beam moves a discrete arcuate distance around the image region during the sampling of each detector subset and further including the step of projecting an effective origin of a fan beam encompassing all positions of the x-ray source during the sampling.

9. The method as set forth in claim 8 wherein the reconstructing step includes convolving each data fan with a convolution function and back projecting the convolved data fans, in the back projecting step, the back projection is conducted using the effective fan origin.

10. A method of tomographic examination comprising:

(a) rotating a fan of penetrating radiation around an image region;

(b) sampling each of a contiguous subset of an arc of radiation detectors to generate a set of electronic data;

(c) repeating step (b) at least once to generate a plurality of data sets;

(d) merging the plurality of data sets into a single data fan;

(e) after the radiation fan has rotated sufficiently that another subset of detectors is irradiated, repeating steps (b) through (d) to generate another data fan;

(f) repeating step (e) to generate a plurality of data fans; and, (g) reconstructing an image representation from the plurality of data fans.

11. The method as set forth in claim 10 further including the steps of monitoring a scanned patient's cardiac cycle at least during step (b), storing the data fans merged in step (d), and retrieving only stored data fans corresponding to a selected portion of the cardiac cycle for reconstruction in step (g).

12. A tomographic scanning apparatus comprising:

a radiation source means for providing a fan beam of penetrating radiation;

a ring of radiation detectors at least partially circumscribing an image region, the radiation source means and the detector ring being disposed relative to each other such that at any one time, the radiation fan beam irradiates a subset of n detectors, where n is an integer;

a rotating means for rotating the radiation fan beam relative to the detector ring such that a plurality of detector subsets are irradiated;

a sampling means for sampling each radiated detector subset a plurality of times during rotation of the fan beam to generate a plurality of data sets, such that each data set is collected with an apex of the fan beam displaced relative to the other data sets collected from a common detector subset;

an interleaving means for intermixing data elements of each of the data sets generated from a common detector subset into a single interleaved data fan;

a reconstruction means for reconstructing a representation of an image of radiation absorption properties of an object in the image region from a plurality of the data fans.

13. The apparatus as set forth in claim 12 further including cardiac synchronizing means for synchronizing sampled data with a scanned patient's cardiac cycle such that the reconstruction means reconstructs an image representation corresponding to a selectable portion of the scanned patient's cardiac cycle.

14. The apparatus as set forth in claim 12 wherein the radiation source includes a single x-ray tube which is rotated by the rotating means.

15. The apparatus as set forth in claim 12 wherein the sampling means samples s sets of data generated by each detector subset, where s is an integer.

16. The apparatus as set forth in claim 15 wherein the interleaving means interleaves the data elements alternately from each data set such that the data elements from the first data set are positioned in each $sz+1$ position of the data fan, where $z$ is an integer from zero through $n-1$.

17. The apparatus as set forth in claim 12 wherein the interleaving means includes a plurality of data set memory means for storing each of the data sets generated by the sampling means and data sorting means for sorting data stored in the data set memory means into a data fan memory means.

18. The apparatus as set forth in claim 17 wherein the data sorting means channels data elements from each data set memory serially into the data fan memory.

19. The apparatus as set forth in claim 18 wherein the plurality of data set memory means includes at least a first data set memory means and a second data set memory means and wherein the sorting means sorts data elements from the first and second data set memory means alternately into the data fan memory means.

20. The apparatus as set forth in claim 17 wherein the plurality of data set memory means includes first, second, third, and fourth data set memory means and wherein the sorting means sorts data elements from the first, second, third, and fourth data set memory means serially into the data fan memory means.

* * * * *